(12) United States Patent
Brown

(10) Patent No.: US 12,702,380 B2
(45) Date of Patent: Aug. 11, 2026

(54) ULTRASOUND PROBE SHEATHING SYSTEM AND METHOD

(71) Applicant: Bard Access Systems, Inc., Salt Lake City, UT (US)

(72) Inventor: Taylor A. Brown, Lehi, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

(21) Appl. No.: 18/905,941

(22) Filed: Oct. 3, 2024

(65) Prior Publication Data

US 2026/0096806 A1 Apr. 9, 2026

(51) Int. Cl.
*A61B 8/00* (2006.01)

(52) U.S. Cl.
CPC .................................. *A61B 8/4455* (2013.01)

(58) Field of Classification Search
CPC .................................................... A61B 8/4455
See application file for complete search history.

(56) References Cited

U.S. PATENT DOCUMENTS

2021/0113184 A1 * 4/2021 Mantri .............. A61B 1/00137

FOREIGN PATENT DOCUMENTS

CN 117357360 A * 1/2024 ......... A61G 13/0018

OTHER PUBLICATIONS

CN-117357360 machine translation (Year: 2024).*

* cited by examiner

*Primary Examiner* — Alexei Bykhovski
(74) *Attorney, Agent, or Firm* — Rutan & Tucker LLP

(57) ABSTRACT

The ultrasound probe cover system comprises a cradle arm supporting an ultrasound probe in a predetermined position, a first applicator arm articulating relative to the cradle arm and housing a sterilizer applicator and a gel applicator for applying a sterilizing agent and a gel to the probe head, and a sheath arm with a sheath holder supporting an open sheath. The sheath arm articulates relative to the cradle arm to position the sheath opening over the probe head. The sheath includes a biasing member extending helically and configured to bias the sheath to an extended configuration to facilitate placing the sheath over the probe. The cover system provides a convenient and efficient solution for covering and preparing ultrasound probes for medical procedures, enhancing hygiene and usability in healthcare settings.

16 Claims, 3 Drawing Sheets

ULTRASOUND PROBE SHEATHING SYSTEM AND METHOD

BACKGROUND

When using an ultrasound probe on a patient various steps should be performed by the clinician in order to clean and sterilize the probe head, apply a sheath or similar sterile barrier to the probe, and apply a gel to facilitate acoustic transmission. Such steps can be time-consuming, require the clinician to have both hands free, and risk the probe falling outside of a sterile field, compromising the sterility of the device and the clinician. Furthermore, because of the time-consuming nature, these steps may not be performed as often as might be required to maintain sterility both within and between procedures.

What is needed therefore is a system and method to allow a clinician to securely retain the probe within a sterile field, automatically sterilize the probe, apply a gel, apply a sheath, or combinations thereof, and with little or no manipulation required of the clinician. This reduces clinician workload, reduces human error and facilitates these processes, motivating more frequent cleaning and gel application of the ultrasound probe.

SUMMARY

In some aspects, the techniques described herein relate to an ultrasound probe cover system including, a cradle arm including a cradle and configured to support an ultrasound probe having a probe head and oriented at a predetermined position, a first applicator arm configured to articulate relative to the cradle arm and includes one or both of a sterilizer applicator and a gel applicator, the sterilizer applicator configured to apply a sterilizing agent and the gel applicator configured to apply a gel to the probe head, when the probe is engaged with the cradle, and a sheath arm having a sheath holder configured to support an opening of a sheath in open configuration, the sheath arm configured to articulate relative to the cradle arm to place the sheath opening over the probe head.

In some aspects, the techniques described herein relate to an ultrasound probe cover system, wherein the cradle engages the probe in one of an interference fit, friction fit, or snap fit engagement to secure the probe in the predetermined position.

In some aspects, the techniques described herein relate to an ultrasound probe cover system, wherein the sterilizing agent includes one or more of a UV sterilization, a liquid sterilizing agent, a vapor sterilizing agent, a gaseous sterilizing agent, a detergent sterilizing agent, and an ethylene oxide gas sterilizing agent, and wherein the gel includes an acoustically conductive gel configured to improve acoustic transmission between the probe head and a skin surface of a patient.

In some aspects, the techniques described herein relate to an ultrasound probe cover system, further including a second applicator arm including the gel applicator, the second applicator arm configured to articulate relative to the cradle arm independently of the first applicator arm.

In some aspects, the techniques described herein relate to an ultrasound probe cover system, wherein one or both of the first applicator arm and the second applicator arm includes a shield coupled thereto and configured to enclose one or more of the sterilizer applicator, the gel applicator, and the probe head when the probe is engaged with the cradle.

In some aspects, the techniques described herein relate to an ultrasound probe cover system, wherein the sheath has a body extending between tip and a base and defines a cavity, the base including the opening communicating with the cavity, the sheath further includes a biasing member extending helically through a wall of the body and biasing the sheath body to a circular cross-sectional shape.

In some aspects, the techniques described herein relate to an ultrasound probe cover system, wherein an inner diameter of the opening and the cavity, when biased to the circular cross-sectional shape is greater than an outer lateral distance of the probe.

In some aspects, the techniques described herein relate to an ultrasound probe cover system, wherein the biasing member biases the sheath body to an extended configuration and is elastically deformable to a collapsed configuration, the tip and the base are disposed further away from each other in the extended configuration relative to the collapsed configuration.

In some aspects, the techniques described herein relate to an ultrasound probe cover system, wherein the sheath further includes a strap configured to retain the sheath body and biasing member in the collapsed configuration.

In some aspects, the techniques described herein relate to an ultrasound probe cover system, wherein the sheath holder is configured to detach the strap as the sheath arm is retracted from the cradle.

In some aspects, the techniques described herein relate to a method of placing a sheath over an ultrasound probe including, engaging the ultrasound probe with a cradle supported by a cradle arm, the ultrasound probe having a probe head, the cradle supporting the probe head at a predetermined position, actuating a first applicator arm to articulate relative to the cradle arm to place one or both of a sterilizer applicator and a gel applicator adjacent the probe head, and actuating a sheath arm, having a sheath holder supporting the sheath, to articulate relative to the cradle arm to place the sheath over the probe head.

In some aspects, the techniques described herein relate to a method, wherein engaging the ultrasound probe with the cradle further includes one of an interference fit, friction fit, or snap fit engagement to secure the probe in the predetermined position.

In some aspects, the techniques described herein relate to a method, further including the sterilizer applicator applying a sterilizing agent and the gel applicator applying a gel to one of the probe head or an outer surface of the sheath when the probe is engaged with the cradle.

In some aspects, the techniques described herein relate to a method, wherein the sterilizing agent includes one or more of a UV sterilization, a liquid sterilizing agent, a vapor sterilizing agent, a gaseous sterilizing agent, and an ethylene oxide gas sterilizing agent, and wherein the gel includes an acoustically conductive gel configured to improve acoustic transmission between the probe head and a skin surface of a patient.

In some aspects, the techniques described herein relate to a method, further including actuating a second applicator arm to articulate relative to the cradle arm independently of the first applicator arm, the second applicator arm including the gel applicator.

In some aspects, the techniques described herein relate to a method, wherein one or both of the first applicator arm and the second applicator arm further includes a shield coupled thereto and encloses one or more of the sterilizer applicator, the gel applicator, and the probe head when the probe is engaged with the cradle.

In some aspects, the techniques described herein relate to a method, wherein the sheath has a body extending between tip and a base and defines a cavity, the base including an opening communicating with the cavity, the sheath further includes a biasing member extending helically through a wall of the body and biasing the sheath body to a circular cross-sectional shape.

In some aspects, the techniques described herein relate to a method, wherein an inner diameter of the opening and the cavity, when biased to the circular cross-sectional shape is greater than an outer lateral distance of the probe.

In some aspects, the techniques described herein relate to a method, wherein the biasing member biases the sheath body to an extended configuration and is elastically deformable to a collapsed configuration, the tip and the base are disposed further away from each other in the extended configuration relative to the collapsed configuration.

In some aspects, the techniques described herein relate to a method, further including disengaging a strap configured to retain the sheath body and the biasing member in the collapsed configuration, by the sheath holder as the sheath arm retracts from the cradle arm.

BRIEF DESCRIPTION OF DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1:
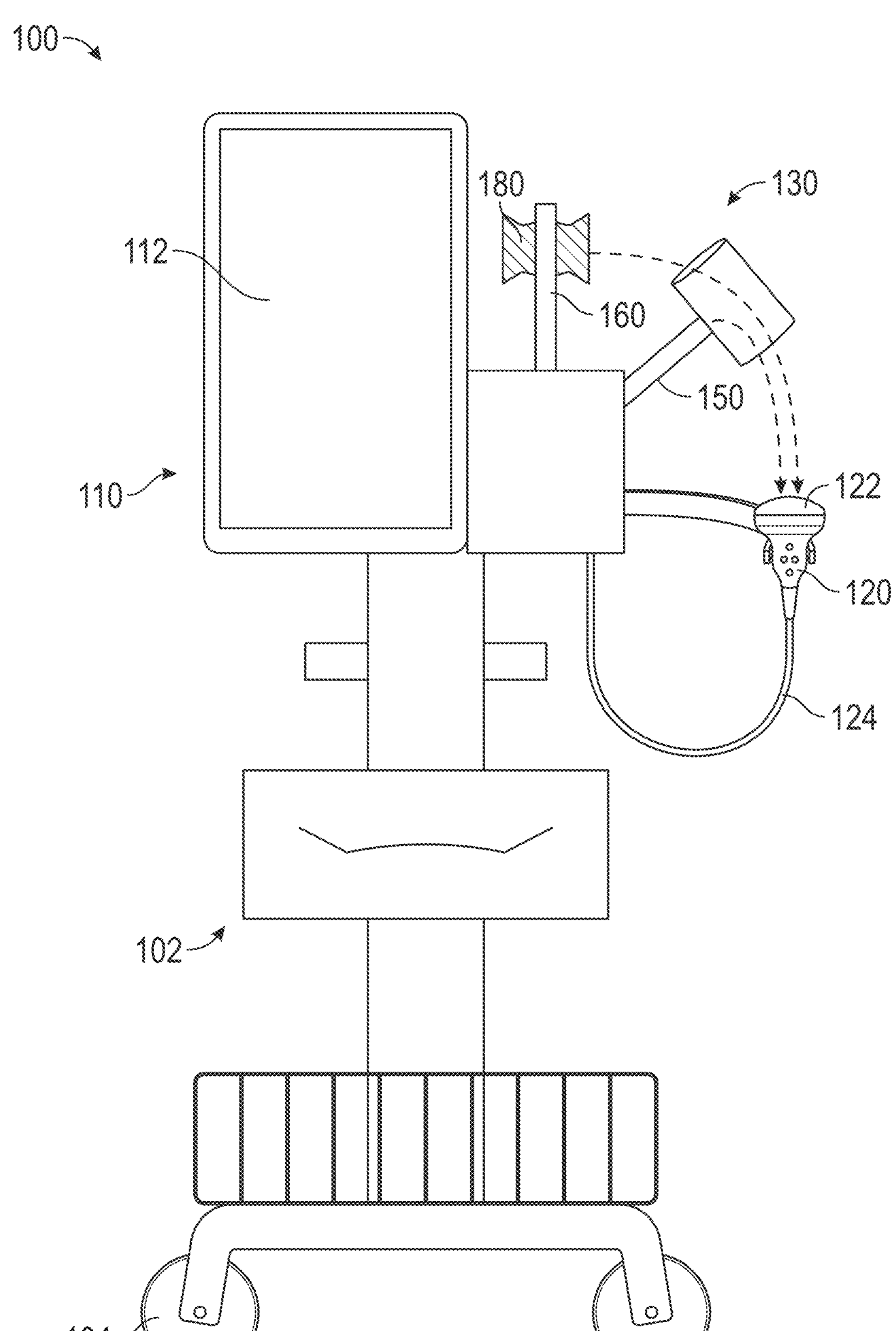
FIG. 1 shows a perspective view of an ultrasound system including an automated cover system, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein. It is understood that the drawings are diagrammatic and schematic representations of exemplary embodiments of the invention and are neither limiting nor necessarily drawn to scale.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "right," "left," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise. Also, the words "including," "has," and "having," as used herein, including the claims, shall have the same meaning as the word "comprising."

In the following description, the terms "or" and "and/or" as used herein are to be interpreted as inclusive or meaning any one or any combination. As an example, "A, B or C" or "A, B and/or C" mean "any of the following, A, B, C, A and B, A and C, B and C, A, B and C." An exception to this definition will occur only when a combination of elements, components, functions, steps or acts are in some way inherently mutually exclusive.

With respect to "proximal," a "proximal portion" or a "proximal end portion" of, for example, a probe or system disclosed herein includes a portion of the probe or system intended to be near, or relatively nearer to, a clinician when the probe or system is used on a patient. Likewise, a "proximal length" of, for example, the probe or system includes a length of the probe or system intended to be near or relatively nearer to the clinician when the probe or system is used on the patient. A "proximal end" of, for example, the probe or system includes an end of the probe or system intended to be near or relatively nearer to the clinician when the probe or system is used on the patient. The proximal portion, the proximal end portion, or the proximal length of the probe or system can include the proximal end of the probe or system; however, the proximal portion, the proximal end portion, or the proximal length of the probe or system need not include the proximal end of the probe or system. That is, unless context suggests otherwise, the proximal portion, the proximal end portion, or the proximal length of the probe or system is not necessarily a terminal portion or terminal length of the probe or system.

With respect to "distal," a "distal portion" or a "distal end portion" of, for example, a probe or system disclosed herein includes a portion of the probe or system intended to be near, or relatively nearer to, a patient when the probe or system is used on a patient. Likewise, a "distal length" of, for example, the probe or system includes a length of the probe or system intended to be near or relatively nearer to the patient when the probe or system is used on the patient. A "distal end" of, for example, the probe or system includes an end of the probe or system intended to be near or relatively nearer to the patient when the probe or system is used on the patient. The distal portion, the distal end portion, or the distal length of the probe or system can include the distal end of the probe or system; however, the distal portion, the distal end portion, or the distal length of the probe or system need not include the distal end of the probe or system. That is, unless context suggests otherwise, the distal portion, the distal end portion, or the distal length of the probe or system is not necessarily a terminal portion or terminal length of the probe or system.

Figure 2:
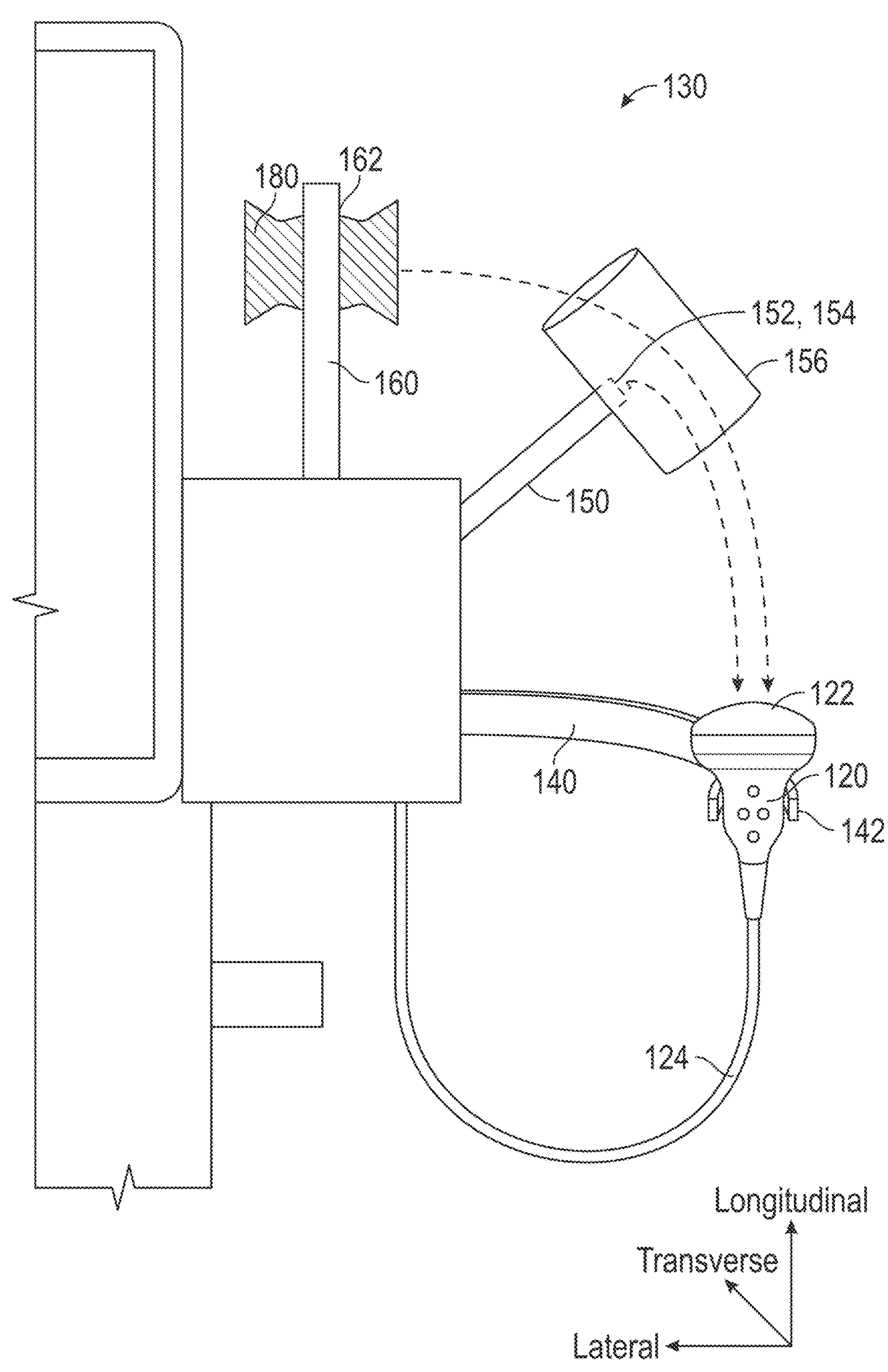
FIG. 2 shows further detail of the automated cover system of FIG. 1, in accordance with embodiments disclosed herein.

To assist in the description of embodiments described herein, as shown in FIG. 2, a longitudinal axis extends substantially parallel to an axial length of the ultrasound probe. A lateral axis extends normal to the longitudinal axis, and a transverse axis extends normal to both the longitudinal and lateral axes.

Unless defined otherwise, all technical and scientific terms used herein have the same meaning as commonly understood by those of ordinary skill in the art.

FIG. 1 shows an exemplary ultrasound system ("system") 100 generally including, a stand 102, a console 110, an ultrasound probe ("probe") 120 and an automated probe cover system ("cover system") 130. The stand 102 is configured to support one or more of the console 110, the probe 120, and the cover system 130. As will be appreciated, other items can be supported by the stand 102 including gloves, acoustic gels, controls, keyboards, etc. Optionally, the stand includes one or more wheels 104 to facilitate moving the system 100 between different locations in a clinical setting.

In an embodiment, the console 110 is communicatively coupled with the probe 120 by either wired or wireless communication, and configured to send and receive information to generate an ultrasonic image that is projected to the user on a display 112 or the like. In an embodiment, the probe 120 includes a probe head 122 including one or more acoustic transducers configured to emit ultrasonic acoustic signals and receive reflected acoustic signals in order to generate an image of a subcutaneous target location. In use, the probe head 122 is placed in contact with a skin surface of a patient to transmit signal waves and received reflected waves. Often an acoustic gel is applied to the probe head 122 to facilitate acoustic transmission between the probe head 122 and the skin surface.

As will be appreciated, when using the probe 120 on a patient, the probe 120 must be cleaned and sterilized between uses. Frequently applying cleaning chemicals directly to the probe 120 can have detrimental effects on the sensitive electronics and ultrasonic transducers. As such, the probe 120 is often placed within a sheath 180 that can provide a sterile barrier between the probe 120 and the patient as well as protect the probe 120 from excessive exposure to cleaning agents.

In an embodiment, the sheath 180 includes a sheath body 194 formed of a thin, woven or non-woven, flexible material that is acoustically transparent such as a plastic, polymer, or similar suitable material. Optionally, the sheath 180 can be transparent or translucent material to facilitate observing and manipulating the probe 120 disposed therein. Placing the probe 120 within the sheath can be a time-consuming task, often requiring the clinician to have both hands free. Further, should the probe 120, the sheath 180, or combinations thereof, fall outside of the sterile area, e.g. fall to the ground, or touch a non-sterile surface, the process of changing the sheath 180 mid-procedure can be a time consuming and complex task. Further this may require the clinician to change gloves, gowns, drapes, or other sterile equipment, escalating costs.

In an embodiment, the cover system 130 is configured to securely retain the probe 120 within the sterile field in an easily accessible manner. Further, the cover system 130 automatically sterilizes the probe 120, the sheath 180, or combinations thereof, applies an acoustic gel to a distal end of the probe 120, the sheath 180, or combinations thereof, and can apply or replace a sheath 180 over the probe 120. In an embodiment, the cover system 130 further includes one or more sensors configured to detect one or more of the probe 120 removed or replaced to cover system 130, sterilizing the probe 120, applying gel to the probe 120, and/or sheathing the probe 120 to record one or more processes of the cover system 130, as described in more detail herein. Advantageously, the cover system 130 can automatically record and log these events for future analysis of the procedure, to ensure standards of care are being maintained, and can track inventory control.

As shown in FIG. 2, the cover system 130 includes a cradle arm 140 extending therefrom and including a cradle 142 configured to releasably retain the probe 120. In an embodiment, the cradle 142 engages the probe 120 in an interference fit, friction fit, or snap-fit engagement. In an embodiment, one or both of the cradle 142 and the probe 120 further includes an engagement mechanism such as a clip, latch, ball and detent, or similar mechanism to releasably secure the probe 120 in the cradle 142.

Advantageously, the cradle 142 secures the probe 120, or more specifically the probe head 122, within the sterile field and in a predetermined position in relation to the cover system 130. Further, the cradle 142 can secure the probe 120 in an easily accessible position and prevent the probe 120 from falling outside of a sterile area. This allows the clinician to quickly and easily place the probe 120 down, reducing the risk of the probe 120 falling, reducing the risk of the probe head 122 touching non-sterile areas, or disturbing any acoustic gel coating applied to the probe head 122.

In an embodiment, the cover system 130 further includes an applicator arm 150 configured to articulate relative to the cradle 142 to place one or more of a sterilizer applicator 152 and a gel applicator 154 adjacent the probe head 122 when the probe 120 is secured within the cradle 142. When placed adjacent to, or in contact with, the probe head 122, the sterilizer applicator 152 can be configured to apply a sterilizing agent to sterilize one or more of the probe head 122, probe 120, a portion of the cable 124, a surface of the sheath 180, or combinations thereof. Exemplary sterilization agents can include a UV sterilization, a liquid sterilizing agent, a vapor sterilizing agent, a gaseous sterilizing agent, a detergent sterilizing agent, an ethylene oxide gas (EtO) sterilizing agent, combinations thereof, or the like. In an embodiment, the applicator arm 150 further includes a shield 156 coupled thereto and configured to enclose one or more of the sterilizer applicator 152, the gel applicator 154, the probe 120, the probe head 122, a portion of the cable 124, the cradle 142, a portion of the cradle arm 140, or combinations thereof, within a cavity defined by the shield 156 to protect surrounding structures, the clinician, or the patient from any detrimental exposure to the sterilizing process, or mess from the gel application process.

In an embodiment, the applicator arm 150 further includes a gel applicator 154 configured to apply a predetermined bolus of ultrasound gel to the probe head 122. The gel applicator 154 can apply the gel before, during, or after sterilization. In an embodiment, the cover system 130 includes a first applicator arm that includes the sterilizer applicator 152 as described herein, and a second applicator arm (not shown) that includes the gel applicator 154. Optionally, one or both of the first applicator arm 150 and the second applicator arm includes a shield 156 as described herein. Advantageously, the shield 156 can protect surrounding structures from any splashes of gel during the gel application process. Advantageously, the gel applicator 154 can apply a predetermined bolus of gel to ensure the correct amount is applied without compromising acoustic conductivity, nor wasting excess gel. In an embodiment, the gel applicator 154 includes a heating element, configured to warm the gel to a predetermined temperature, e.g. a similar temperature to that of the skin surface of a patient. In an embodiment, the clinician can modify the predetermined temperature by providing an input to the console 110.

In an embodiment, the cover system 130 further includes a sheath arm 160 having a sheath holder 162 and configured to articulate relative to the cradle 142 to place one or more sheaths 180 over one or more of the probe head 122, probe 120, and a portion of the cable 124. As shown, one or more of the applicator arm 150 and the sheath arm 160 are shown to pivot relative to the cradle arm 140 to place one of the sterilizer applicator 152, gel applicator 154, and/or sheath holder 162 in proximity to the probe 120 and pivot in an opposite direction to remove the sterilizer applicator 152, gel applicator 154, and/or sheath holder 162 to prevent obstructing access to the probe 120. As will be appreciated, similar mechanisms of applying and removing the sterilizer applicator 152, gel applicator 154, and/or sheath holder 162 are also contemplated such as linear moving arms, circular moving arms, or the like. In an embodiment, one or more of the applicator arm 150 and the sheath arm 160 remain stationary and the cradle arm 140 is articulated to engage one or more of the sterilizer applicator 152, gel applicator 154, and/or sheath holder 162, as described herein.

In an embodiment, the sheath arm 160 includes a sheath holder 162 configured to releasably retain one or more sheaths 180. As the sheath arm 160 articulates relative to the cradle 142, the sheath holder 162 places a sheath 180 over one or more of the probe head 122, the probe 120, and a portion of the cable 124. In an embodiment, the sheath arm 160 and sheath holder 162 articulates to engage a sheath 180 already disposed over the probe 120 and remove the old sheath 180 from the probe 120. Optionally, the applicator arm 150 can articulate before or after the new sheath 180 is disposed over the probe 120. In an embodiment, the sheath holder 162, once retracted from the probe 120 and removing the old sheath 180 can disposed the old sheath in a suitable disposal receptacle before engaging a new, clean sheath 180.

Figure 3A:
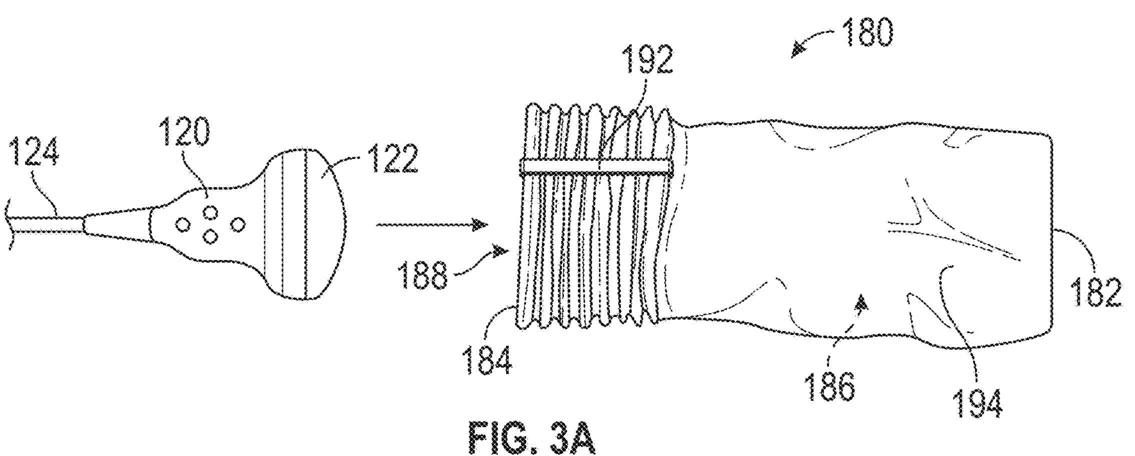
FIGS. 3A-3C shows an exemplary method of applying a sheath having a biasing member to a probe of an ultrasound system, in accordance with embodiments disclosed herein.
Figure 3B:
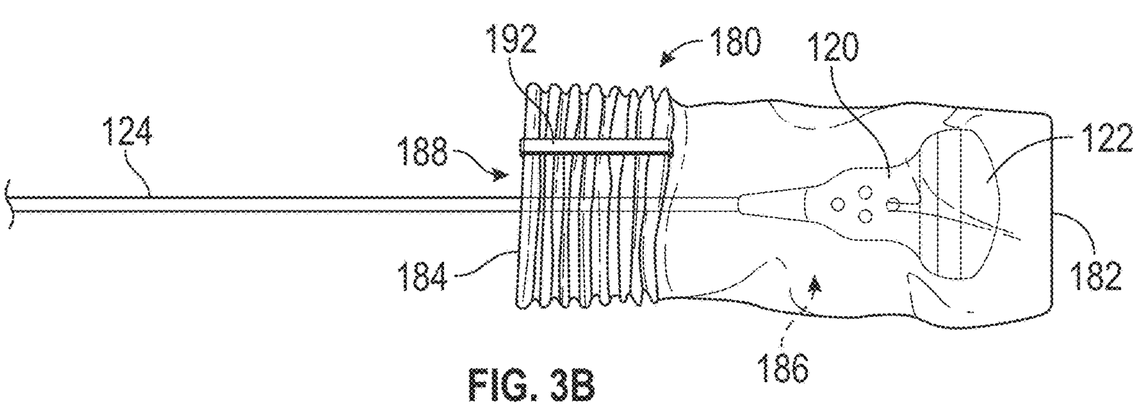
Figure 3C:
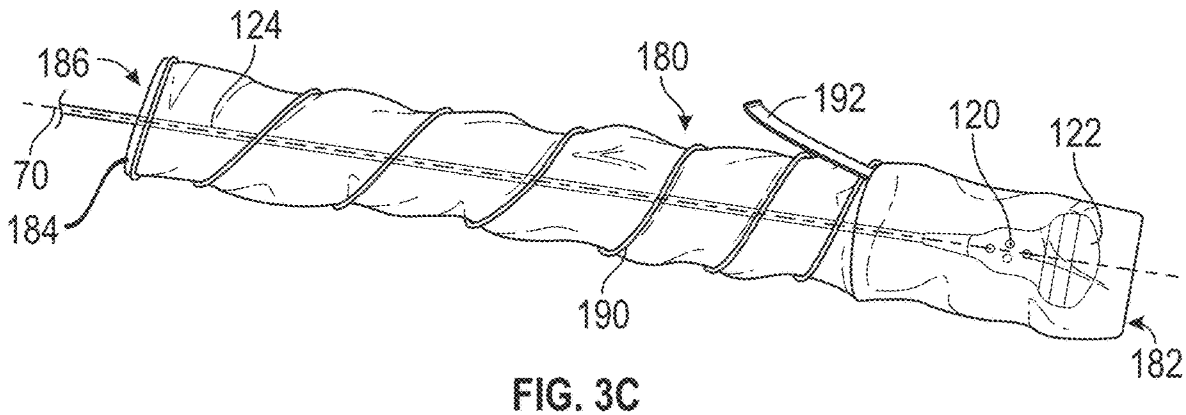

FIGS. 3A-3C show further details of the sheath 180. In an embodiment, the sheath 180 includes a body 194 is formed of a flexible material and extends from a tip 182 to a base 184. The sheath body 194 forms a cavity 186 communicating with an opening 188 at the base 184. The cavity 186 and the opening 188 is sized to receive the probe 120 therein. In an embodiment, a diameter of the cavity 186 and the opening 188 is larger than an outer lateral or transverse dimension of the probe 120, where the probe 120 extends along a longitudinal axis between the probe head 122 and the cable 124.

As shown in FIG. 3A, the probe 120 can be placed through the opening 188 and the probe head 122 can be placed adjacent the sheath tip 182 within the cavity 186. As shown in FIGS. 3B-3C, the sheath base 184 can then extend over the probe head 122, probe 120 and at least a portion of the cable 124 to enclose these portions within the cavity 186 and provide a sterile barrier. As shown in FIG. 3A, in an embodiment, the sheath 180 is formed of a flexible material that can transition to a collapsed configuration to place the opening at the base 184 relatively closer to the tip 182 and facilitate placing the probe head 122 adjacent the tip 182. Transitioning the sheath 180 to the collapsed configuration often requires the clinician to use two hands to arrange the sheath 180 as shown in FIG. 3A. Holding the sheath in the collapsed configuration, the clinician then needs to place the probe 120 inside the cavity 186 without compromising the sterility of the probe 120.

In an embodiment, a portion of the sheath 180 includes a biasing member 190, such as a wire or similar flexible elongate member disposed within a wall of the sheath body 194 and biased to a linear configuration. The biasing member 190 extends through the sheath wall along a helical path. In an embodiment, the biasing member 190 is disposed within a lumen extending through the wall of the sheath body 194 along a helical path relative to a central longitudinal axis 70 of the sheath 180. In an embodiment, the sheath body 194 includes sleeve coupled to an inner or outer surface of the sheath body 194 and extending through a helical path to secure the biasing member to the sheath 180.

In an embodiment, the biasing member 190 extends over the entire sheath body 194 between the tip 182 and the base 184. In an embodiment, the biasing member 190 extends over a portion of sheath body 194 disposed between the tip 182 and the base 184. For example, as shown in FIG. 3C, the biasing member extends from the base 184 to point disposed between the base 184 and the tip 182, leaving a portion of the sheath body 194 adjacent the tip 182 without any biasing member 190. This allows the clinician to grasp and manipulate the probe 120 without the biasing member 190 affecting the shape of this portion of the sheath 180.

In either of the collapsed configuration (FIG. 3B) and the expanded configuration (FIG. 3C) the biasing member 190 urges the sheath 180 towards a circular cross-sectional shape which facilitates placing probe 120 towards the tip 182 of the sheath. The biasing member 190 is further configured to bias the sheath 180 towards an expanded configuration (FIG. 3C). In an embodiment, the sheath further includes a strap 192 or similar retaining means such as a clasp, latch, or the like, and configured to retain the sheath 180 and biasing member 190 assembly in the collapsed configuration. Advantageously, the strap 192 can retain the sheath 180 and biasing member 190 assembly in the collapsed configuration to facilitate placing the probe head 122 at the tip 182 of the sheath 180. Once the probe 120 has been placed at the tip 182 of the sheath 180 the strap 192 can be released to allow the biasing member 190 to urge the base 184 of the sheath 180 to the expanded configuration (FIG. 3C).

In an exemplary method of use, an ultrasound system 100 is provided, as described herein, including a cover system 130. A clinician places the probe 120 of the ultrasound system 100 in the cradle 142. The cradle 142 releasably retains the probe 120 in a predetermined position. As shown in FIG. 1, the probe 120 is retained in a vertical position with the probe head 122 extending upwards from the cradle 142. It will be appreciated, however, that other predetermined positions and orientations are also contemplated to fall within the scope of the present invention.

In an embodiment, the cover system 130 is activated by trigger. Exemplary triggers can include receiving an input from the clinician, detecting the probe 120 engaged with the cradle 142 using one or more sensors, a time-based trigger where the cover system 130 is activated at a predetermined time interval, combinations thereof, or the like. In an embodiment, the method further includes actuating an applicator arm 150 to articulate relative to the cradle 142 and place one or both of a sterilizer applicator 152 and a gel applicator 154 in contact with the probe head 122 or a surface of a portion of the sheath 180 disposed over the probe head 122.

In an embodiment, the method further includes actuating a sheath arm 160 to articulate relative to the cradle 142 and remove a sheath 180 from and/or place a sheath 180 over the probe head 122. In an embodiment, the applicator arm 150 is actuated before the sheath arm 160, after the sheath arm 160, or both. In an embodiment, the sheath 180 includes a biasing member 190 extending through at least a portion of the sheath body 194 in a helical shape and biasing the sheath 180 to one or both of a circular cross-sectional shape and an extended configuration where the base 184 is disposed relatively further from the sheath tip 182.

In an embodiment, as the sheath arm 160 is retracted from the cradle arm 140, the sheath holder 162 detaches a strap 192 to release the biasing member 190 and allow the sheath 180 to extend over the probe 120 and portion of the cable 124. In an embodiment, as the probe 120 is detached from cradle 142, the cradle 142 is configured to detach the strap 192 to release the biasing member 190 and allow the sheath 180 to extend over the probe 120 and portion of the cable 124. In an embodiment, the clinician can grasp the probe 120 and release the strap 192 to release the biasing member 190 and allow the sheath 180 to extend over the probe 120 and portion of the cable 124.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An ultrasound probe cover system, comprising:

a cradle arm including a cradle and configured to support an ultrasound probe having a probe head and oriented at a predetermined position;

a first applicator arm configured to articulate relative to the cradle arm and including a sterilizer applicator, the sterilizer applicator configured to apply a sterilizing agent to the probe head when the ultrasound probe is engaged with the cradle;

a second applicator arm including a gel applicator and configured to articulate relative to the cradle arm independently of the first applicator arm to apply a gel to the probe head when the ultrasound probe is engaged with the cradle, wherein one or both of the first applicator arm and the second applicator arm including a shield coupled thereto and configured to enclose one or more of the sterilizer applicator, the gel applicator, and the probe head when the ultrasound probe is engaged with the cradle; and a sheath arm having a sheath holder configured to support an opening of a sheath in open configuration, the sheath arm configured to articulate relative to the cradle arm to place the opening of the sheath over the probe head.

2. The ultrasound probe cover system according to claim 1, wherein the cradle engages the ultrasound probe in one of an interference fit, a friction fit, or a snap fit engagement to secure the ultrasound probe in the predetermined position.

3. The ultrasound probe cover system according to claim 1, wherein the sterilizing agent includes one or more of a UV sterilization, a liquid sterilizing agent, a vapor sterilizing agent, a gaseous sterilizing agent, a detergent sterilizing agent, and an ethylene oxide gas sterilizing agent, and wherein the gel includes an acoustically conductive gel configured to improve acoustic transmission between the probe head and a skin surface of a patient.

4. The ultrasound probe cover system according to claim 1, wherein the sheath has a body extending between tip and a base and defines a cavity, the base including the opening communicating with the cavity, the sheath further includes a biasing member extending helically through a wall of the body and biasing the body of the sheath to a circular cross-sectional shape.

5. The ultrasound probe cover system according to claim 4, wherein an inner diameter of the opening and the cavity, when biased to the circular cross-sectional shape is greater than an outer lateral distance of the ultrasound probe.

6. The ultrasound probe cover system according to claim 4, wherein the biasing member biases the body of the sheath to an extended configuration and is elastically deformable to a collapsed configuration, the tip and the base are disposed further away from each other in the extended configuration relative to the collapsed configuration.

7. The ultrasound probe cover system according to claim 6, wherein the sheath further includes a strap configured to retain the body of the sheath and the biasing member in the collapsed configuration.

8. The ultrasound probe cover system according to claim 7, wherein the sheath holder is configured to detach the strap as the sheath arm is retracted from the cradle.

9. A method of placing a sheath over an ultrasound probe, comprising:

engaging the ultrasound probe with a cradle supported by a cradle arm, the ultrasound probe having a probe head, the cradle supporting the probe head at a predetermined position;

actuating a first applicator arm to articulate relative to the cradle arm to place a sterilizer applicator adjacent the probe head;

actuating a second applicator arm to articulate relative to the cradle arm independently of the first applicator arm, to place a gel applicator adjacent the probe head, wherein one or both of the first applicator arm and the second applicator arm includes a shield coupled thereto and encloses one or more of the sterilizer applicator, the gel applicator, and the probe head when the ultrasound probe is engaged with the cradle; and actuating a sheath arm, having a sheath holder supporting the sheath, to articulate relative to the cradle arm to place the sheath over the probe head.

10. The method according to claim 9, wherein engaging the ultrasound probe with the cradle further includes one of an interference fit, a friction fit, or a snap fit engagement to secure the ultrasound probe in the predetermined position.

11. The method according to claim 9, further including the sterilizer applicator applying a sterilizing agent and the gel applicator applying a gel to one of the probe head or an outer surface of the sheath when the ultrasound probe is engaged with the cradle.

12. The method according to claim 11, wherein the sterilizing agent includes one or more of a UV sterilization, a liquid sterilizing agent, a vapor sterilizing agent, a gaseous sterilizing agent, and an ethylene oxide gas sterilizing agent, and wherein the gel includes an acoustically conductive gel configured to improve acoustic transmission between the probe head and a skin surface of a patient.

13. The method according to claim 9, wherein the sheath has a body extending between tip and a base and defines a cavity, the base including an opening communicating with the cavity, the sheath further includes a biasing member extending helically through a wall of the body and biasing the body of the sheath to a circular cross-sectional shape.

14. The method according to claim 13, wherein an inner diameter of the opening and the cavity, when biased to the circular cross-sectional shape is greater than an outer lateral distance of the ultrasound probe.

15. The method according to claim 13, wherein the biasing member biases the body of the sheath to an extended configuration and is elastically deformable to a collapsed configuration, the tip and the base are disposed further away from each other in the extended configuration relative to the collapsed configuration.

16. The method according to claim 15, further including disengaging a strap configured to retain the body of the sheath and the biasing member in the collapsed configuration, by the sheath holder as the sheath arm retracts from the cradle arm.

* * * * *